(12) United States Patent
Chen et al.

(10) Patent No.: US 10,168,141 B2
(45) Date of Patent: Jan. 1, 2019

(54) METHOD FOR IDENTIFYING AIR POLLUTION SOURCES BASED ON AEROSOL RETRIEVAL AND GLOWWORM SWARM ALGORITHM

(71) Applicant: University of Electronic Science And Technology of China, Chengdu, Sichuan (CN)

(72) Inventors: Yunping Chen, Sichuan (CN); Ling Tong, Sichuan (CN); Weihong Han, Sichuan (CN); Wenhuan Wang, Sichuan (CN); Chuanqi Zhong, Sichuan (CN); Jiaming Liang, Sichuan (CN); Jia Huang, Sichuan (CN)

( * ) Notice: Subject to any disclaimer, the term of this patent is extended or adjusted under 35 U.S.C. 154(b) by 17 days.

(21) Appl. No.: 15/358,828

(22) Filed: Nov. 22, 2016

(65) Prior Publication Data
US 2017/0184393 A1   Jun. 29, 2017

(30) Foreign Application Priority Data

Dec. 24, 2015   (CN) .......................... 2015 1 0982201

(51) Int. Cl.
| | |
|---|---|
| *G01P 5/00* | (2006.01) |
| *G01B 11/00* | (2006.01) |
| *G06T 7/62* | (2017.01) |
| *G01N 33/00* | (2006.01) |
| *G01P 13/02* | (2006.01) |
| *G06T 7/73* | (2017.01) |

(52) U.S. Cl.
CPC ....... *G01B 11/002* (2013.01); *G01N 33/0034* (2013.01); *G01P 5/00* (2013.01); *G01P 13/02* (2013.01); *G06T 7/62* (2017.01); *G06T 7/73* (2017.01); *G06T 2207/10032* (2013.01); *G06T 2207/20021* (2013.01); *G06T 2207/20076* (2013.01); *G06T 2207/30184* (2013.01); *G06T 2207/30192* (2013.01)

(58) Field of Classification Search
CPC .......... G01B 11/002; G01T 7/62; G01T 7/73; G01T 2207/30192; G01T 2207/30184; G01T 2207/20076; G01T 2207/20021; G01T 2207/10032; G01N 33/0034; G01P 13/02; G01P 5/00
See application file for complete search history.

(56) References Cited

PUBLICATIONS

Jayakumar et al., Glowworm Swarm Optimization Algorithm with Topsis for Solving Multiple Objective Environmental Economic Dispatch Problem, Jul. 4, 2014, Applied Soft Computing 23, pp. 375-386.*

(Continued)

*Primary Examiner* — Toan Le
(74) *Attorney, Agent, or Firm* — Billion & Armitage; Michael A. Collins (57) ABSTRACT

Techniques for identifying air pollution sources based on aerosol retrieval and a glowworm swarm algorithm are described herein. According to these techniques, a satellite remote sensing image is obtained and a wind speed vector is obtained from the satellite remote sensing image. A GSO algorithm is applied, introducing a glowworm similarity correction factor obtained from an attribute value and a wind speed and wind direction correction factor obtained from the wind speed vector, and pollution sources are identified.

7 Claims, 6 Drawing Sheets

(56) References Cited

PUBLICATIONS

McGill et al., Robot Algorithms for Localization of Multiple Emission Sources, Apr. 2011, ACM Computing Surveys, vol. 43, No. 3, Article 15, 25 pp.*

Menon et al., Simultaneous Source Localization and Boundary Mapping for Contaminants, Jun. 27-29, 2012, American Control Conference, Fairmont Queen Elizabeth, Montreal , Canada, pp. 4174-4179.*

* cited by examiner

METHOD FOR IDENTIFYING AIR POLLUTION SOURCES BASED ON AEROSOL RETRIEVAL AND GLOWWORM SWARM ALGORITHM

TECHNICAL FIELD

The present invention relates to the technical field of air pollution source identification, and more particularly to a method for identifying air pollution sources based on aerosol retrieval from remote sensing images and an improved glowworm swarm optimization (GSO) algorithm.

BACKGROUND ART

Air pollution is a serious environment problem currently faced by many countries. Air pollutants including PM2.5 not only reduce air visibility but also influence outdoor activities. Moreover, studies have shown that PM2.5 can directly enter lower respiratory tract of a human body, and may be closely related to respiratory diseases and heart diseases. The respiratory diseases currently show a rising trend in China, which attracts much attention.

The most important thing in preventing air pollution is pollution source control. A premise for performing subsequent management is to locate emission sources of the air pollutants, and to determine their emission amounts; such information means a lot to decision makers.

Conventionally, two methods are used to trace sources of the air pollutants. The first is a backward tracing method based on ground sampling. This method performs on-site ground pollutant sampling and then analyzes chemical ingredients of the samples in laboratories. Then sources of the pollutants are determined based on the chemical ingredients of the pollutants. The most typical approach adopting this method is a receptor model, which is also the most widely used method for tracing pollutant sources currently. The other is a forward tracing method based on an emission inventory and a diffusion model. This method puts an acquired emission inventory into a diffusion model to simulate movement of the pollutants. This method is most suitable for pollution prediction. Both the methods have their advantages and disadvantages. For the backward tracing method, a large amount of on-site sampling and laboratory analysis are required, which makes the workload heavy and the cost high, making it difficult to be used in large scale and continuously. Instead, it is only discontinuously used in some very important areas. As for the forward tracing method, the emission inventory plays a very important role. Unfortunately, up till now there is no complete emission inventory available in China. Moreover, unclear classification of the emission sources and lack of emission factors database make it hardly possible to set up an emission inventory in some situations.

With the rapid development of space technologies, the capability and precision of acquiring ground surface spatial information are greatly improved. Satellite remote sensing data is tremendously improved in terms of their temporal resolution, spatial resolution and resolution. It has been proved feasible to use satellite remote sensing images to quantitatively acquire physical and chemical properties of the ground surface or air. With the further improvement of research and improvement of algorithms, the precision of quantitative retrieval is constantly improved. There have been a lot of researches in using remote sensing images to estimate concentration of the air pollutants and to analyze distribution of the air pollutants. A problem to be solved is how to use the periodically acquired satellite remote sensing images obtained at a low cost but having a big space coverage area to address the problem of tracing sources of pollutants.

DISCLOSURE OF THE INVENTION

An object of the present invention is to provide a method for identifying air pollution sources based on aerosol retrieval and a Glowworm Swarm Optimization (GSO) algorithm. The GSO algorithm is used to trace pollution sources from an Aerosol Optical Depth (AOD) image retrieved from a satellite remote sensing image, thereby effectively and accurately identifying the air pollution sources.

In order to meet the above objective of the invention, the method for identifying air pollution sources based on the aerosol retrieval and the GSO algorithm of the present invention comprises the following steps:

S1: acquiring a satellite remote sensing image and a digital map including a region corresponding to the satellite remote sensing image;

S2: acquiring a wind direction and a wind speed of the region corresponding to the satellite remote sensing image, to obtain a wind speed vector $\overrightarrow{speed}_{wind}$;

S3: retrieving AOD values from the satellite remote sensing image, to obtain an AOD result image;

S4: gridding the AOD result image, wherein a length of a side of a grid is set as needed.

In this step, the AOD result image is partitioned into M×N image blocks, an average AOD value of pixels included in each image block is calculated. At the same time, the digital map of the region corresponding to the satellite remote sensing image is gridded, and partitioned into M×N image blocks. Coordinates $E_k$ of an image block corresponding to an enterprise k are obtained based on enterprise coordinates, k=1, 2, ..., K, and K is the number of enterprises;

S5: tracing pollutant sources using a method based on improved GSO, which comprises steps of:

S5.1: setting an initial luciferin level $L_i(0)$ of each glowworm to be the same, taking coordinates of each pixel block as an initial location $x_i(0)$ of the glowworm, taking the average AOD value corresponding to the pixel blocks as an attribute value $A_i$ of the glowworm, and setting an initial value $r_d^i(0)$ of a neighborhood of each glowworm, i=1, 2, ..., Q, Q=M×N;

S5.2: letting an iteration number t=1;

S5.3: calculating a luciferin level of a glowworm i of a t-th generation according to the following equation:

$$L_i(t)=(1-\rho)L_i(t-1)+\gamma F(x_i(t))$$

where t is the iteration number, i is an index of the glowworm, $L_i(t)$ is a luciferin level of a glowworm i of the t-th generation, $L_i(t-1)$ is a luciferin level of the glowworm i of a (t−1)-th generation, $\rho$ is a luciferin decay constant, $\rho\in(0, 1)$, $\gamma$ is a luciferin enhancement constant, $F(x_i(t))$ represents an objective function value of the glowworm i at a current location $x_i(t)$, and the objective function is calculated according to the following equation:

$$F(x_i(t)) = \sum_{k=1}^{K} \frac{1}{d_{ik}(t)}$$

where $d_{ik}(t)$ is a distance between the glowworm i at the current location $x_i(t)$ and the coordinates $E_k$ of the enterprise k;

S5.4: for each glowworm i, calculating a moving probability $p_{ij}(t)$ to another glowworm j in a neighborhood $N_i(t)$ thereof; selecting the glowworm j, to which the glowworm i is to move for this time, using the roulette rule, and marking with an index j', and then updating the location of the glowworm i according to the following equation:

$$x_i(t+1) = x_i(t) + s\left(\frac{x_{j'}(t) - x_i(t)}{\|x_{j'}(t) - x_i(t)\|}\right) + \Delta_{attribute} + \Delta_{wind}$$

where $x_{j'}(t)$ is a location of the glowworm j' of the t-th generation, s is a moving step size, and $\|\ \|$ represents solving an Euclidean norm;

$\Delta_{attribute}$ is a glowworm similarity correction factor calculated as follows: firstly in a neighborhood $N_i(t)$ of the glowworm i, a glowworm j* with a closest attribute value $A_i$ to the glowworm i is searched and then $\Delta_{attribute}$ is calculated:

$$\Delta_{attribute} = s_a \cdot \left(\frac{x_{j*}(t) - x_i(t)}{\|x_{j*}(t) - x_i(t)\|}\right)$$

where $s_a$ is a predetermined step size, $x_{j*}(t)$ is a location of the glowworm j* of the t-th generation;

$\Delta_{wind}$ is a wind speed and wind direction correction factor, and calculated as: $\Delta_{wind} = s_w \cdot \overrightarrow{speed}_{wind}$, where $s_w$ is a scaling factor;

S5.5: in condition that the iteration number t=T, T representing a maximum predetermined iteration number of times, taking a current location of each glowworm as a source location $x_i^0$ thereof, and terminating the iteration; otherwise proceeding to step S5.6;

S5.6: updating a neighborhood radius $r_d^i(t+1)$ of each glowworm, then letting t=t+1, and returning to step S5.3;

S6: obtaining a radius $R_k$ of a pollution coverage area of the enterprise according to the coordinates $E_k$ of the image block corresponding to the enterprise;

S7: according to the radius $R_k$ of the pollution coverage area and the source location $x_i^0$ of each glowworm, taking the enterprise k as an enterprise producing pollutants corresponding to the glowworms in the pollution coverage area thereof, calculating an AOD value corresponding to the glowworms in the pollution coverage area thereof as a pollution index of the enterprise k.

In the method for identifying air pollution sources based on aerosol retrieval and the glowworm swarm optimization algorithm in the present invention, firstly AOD values are retrieved from a satellite remote sensing image, and a wind speed vector of a corresponding region is obtained. Next the satellite remote sensing image and the digital map of the corresponding region are gridded, to obtain an average AOD value of each image block and coordinates of an image block corresponding to the enterprise. Then, the coordinates of each image block are taken as an initial location of the glowworm in the improved GSO algorithm, and the average AOD value is taken as the attribute of the glowworm, performing iteration. When the location of the glowworm is updated each time, a glowworm similarity correction factor obtained from the attribute value and a wind speed and wind direction correction factor obtained from the wind speed vector are introduced, to obtain a source location of the glowworm after several iteration. Then a radius of a pollution coverage area of the enterprise is calculated, and the enterprise is taken as the enterprise producing pollutants corresponding to the glowworms in the pollution coverage area thereof, thereby identifying the pollution sources.

The present invention has the following beneficial effects:

(1) Source locations of the pollutants are accurately, effectively obtained through an iteration by using the improved GSO;

(2) When updating the glowworm location using the GSO, a glowworm similarity correction factor obtained from the attribute value and a wind speed and wind direction correction factor obtained from the wind speed vector are introduced, which makes the GSO fit better to actual applications of the present invention. As a result, the iteration results are more realistic, improving accuracy of identification of the pollution sources;

(3) The present invention uses only the remote sensing information and geographic information system of enterprises to quantize the pollution situation of each enterprise, without the need for the extremely expensive sample testing and inefficient emission inventory required by conventional arts, thereby effectively and accurately realizing air pollution identification at a low cost.

DETAILED DESCRIPTION OF EMBODIMENTS

In the following, specific embodiments of the present invention will be described in detail with reference to the accompanying drawings such that a person skilled in the art can better understand the invention. In the following description, it is noted that well-known functions and configurations are not described in detail to avoid obscuring the present invention.

Examples

Figure 1:
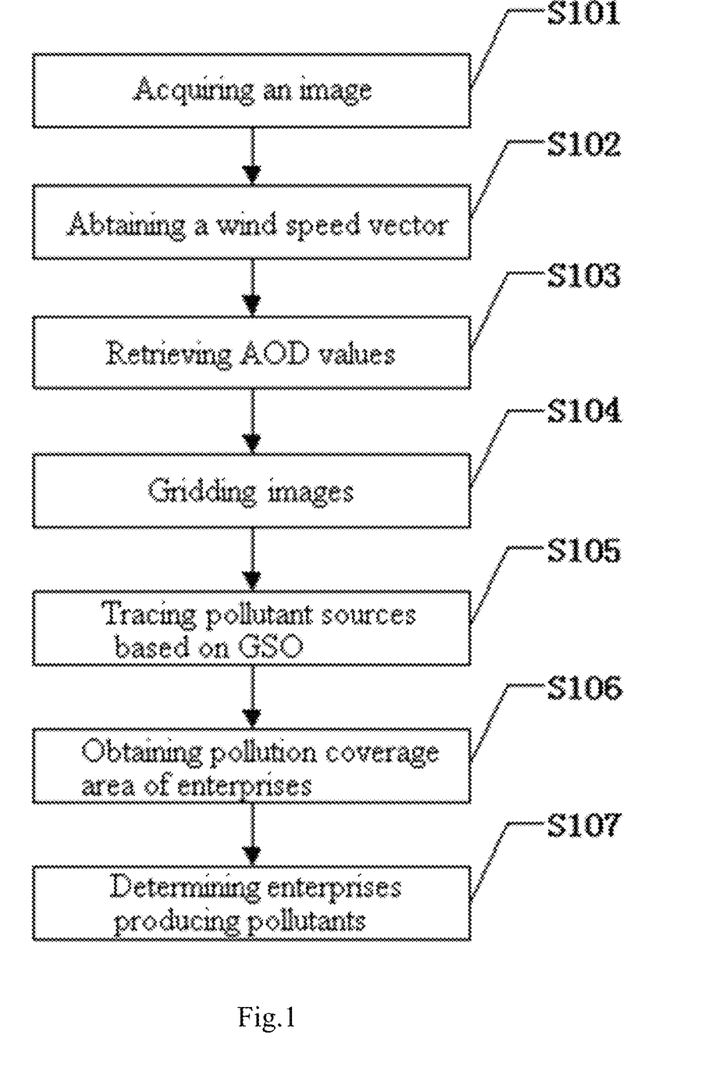
FIG. 1 is a flow chart of an embodiment of a method for identifying air pollution sources based on aerosol retrieval and an improved GSO algorithm.

FIG. 1 is a flow chart of an embodiment of a method for identifying air pollution sources based on aerosol retrieval using the remote sensing technology and the improved GSO algorithm. As shown in FIG. 1, the method for identifying air pollution sources based on aerosol retrieval using the remote sensing technology and the improved GSO algorithm of the present invention comprises the following steps:

S101: acquiring an image:

Firstly, a satellite remote sensing image and a digital map of a corresponding region are acquired. The remote sensing image generally is a multispectral and hyperspectral remote sensing image. The digital map of the region comprises location information of various enterprises which need to be monitored.

S102: acquiring a wind speed vector:

A wind direction and a wind speed of the region corresponding to the satellite remote sensing image are acquired, to obtain a wind speed vector $\overrightarrow{speed}_{wind}$. In the present invention, a pointing direction of the wind speed vector $\overrightarrow{speed}_{wind}$ is a coming direction of the wind.

S103: retrieving AOD (AOD) values:

The AOD values are retrieved from the satellite remote sensing image, obtaining an AOD result image, with a value of each pixel being an AOD value. In the present invention, the AOD value serves as a quantitative reference of air pollutants. Currently, the AOD values can be retrieved by way of a dark dense vegetation (DDV) algorithm, a structure function algorithm, a multidirectional polarized algorithm and so on, which may be selected as needed, and details of the above methods will not be elaborated herein. Generally, there are still blank areas in the AOD result image after retrieval, and the AOD values of the blank areas can be obtained by using an interpolation method.

S104: gridding the image:

The AOD result image is gridded. A length of a grid is set as needed. The AOD result image is partitioned into M×N image blocks, and an average AOD value of pixels included in each image block is calculated, and represented as A(m, n), where m=1, 2, . . . , M, n=1, 2, . . . , N.

In the meantime, the digital map of the region corresponding to the satellite remote sensing image is also gridded. Similarly, the digital map of the region is also partitioned into M×N image blocks. Coordinates $E_k$ of an image block corresponding to an enterprise k are obtained based on enterprise coordinates, k=1, 2, . . . , K, where K indicates a number of the enterprises.

S105: tracing pollution sources based on GSO:

GSO, i.e. Glowworm Swarm Optimization, is a novel metaheuristic optimization method proposed by Krishnanand and Ghose. In GSO, each glowworm is regarded as one solution of a solution space, and each artificial glowworm carries a certain amount of luciferin, emits a certain amount of fluorescence and has its respective visual field, i.e. a decision domain. A size of the luciferin is related to an objective function of its own location, the brighter a glowworm is, the better its location is, and the better the corresponding objective function value is. Each glowworm moves towards a relatively bright glowworm in its neighborhood. Finally, the glowworms are aggregated at preferable locations, and a plurality of extreme points are found, thereby optimizing the swarm. The GSO algorithm is currently a common optimization algorithm, and its specific flow will not be elaborated herein.

In the original GSO algorithm, the movement of one glowworm depends on the luciferin, while the luciferin is determined by the objective function value and the location of the glowworm. The original algorithm does not take attributes of respective glowworms into consideration. However, in the present invention, the AOD value A(m, n) of each image block is taken as an attribute of the glowworm. This attribute is an important factor affecting the movement of the glowworms, which is due to points having the same AOD level are more likely to be derived from the same pollution source. Besides, wind is another important factor, as wind can affect spread of the pollutants. In this sense, the influence of the wind power needs to be considered when tracing the pollution source. Based on the above factors, the present invention proposes a GSO-based method for tracing pollution sources on the basis of the conventional GSO algorithm.

Figure 2:
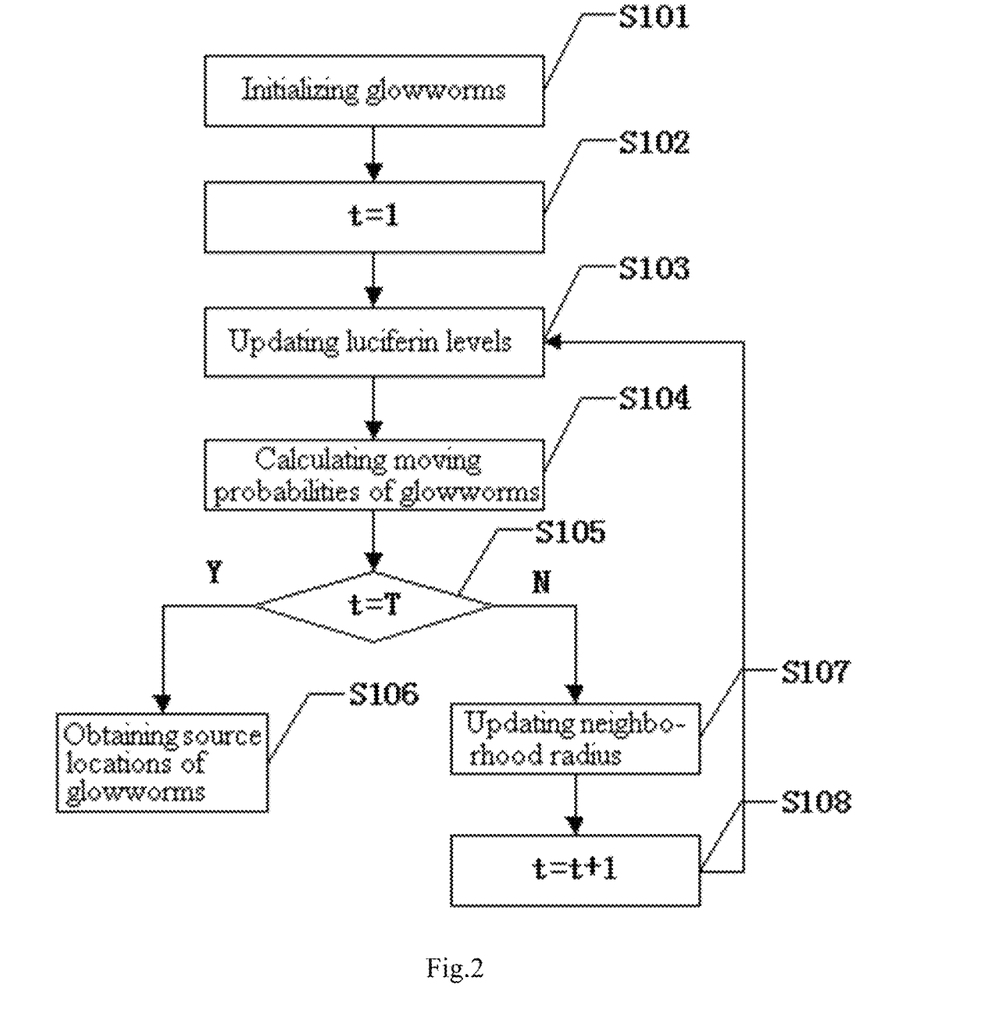
FIG. 2 is a flow chart of a method of tracing pollution source based on GSO in the present invention.

FIG. 2 is a flow chart of a method for tracing pollution sources based on GSO in the present invention. As shown in FIG. 2, the method for tracing pollution sources based on GSO includes:

S201: initializing glowworms:

The present invention is different from the conventional GSO algorithm which randomly initializes glowworms in that each pixel block is taken as one glowworm, an initial luciferin value $L_i(0)$ of each glowworm is set to be the same, coordinates (m, n) of each pixel block are used as an initial location $x_i(0)$ of the glowworm, and an average AOD value A(m, n) corresponding to the pixel block is taken as an attribute value $A_i$ of the glowworm. Moreover, an initial value $r_d^i(0)$ of a neighborhood of respective glowworms and other parameters needed for the GSO algorithm are also set in advance. Apparently, the number of the glowworms in the present invention is Q=M×N, 1=1, 2, . . . , Q.

S202: setting an iteration number t=1;

S203: updating the luciferin:

The luciferin level of a glowworm I of a t-th generation is calculated according to the following equation:

$$L_i(t)=(1-\rho)L_i(t-1)+\gamma F(x_i(t))$$

where t represents the iteration number, i represents an index of the glowworm, $L_i(t)$ represents a luciferin of a glowworm i of the t-th generation, $L_i(t-1)$ represents a luciferin of the glowworm i of a (t-1)-th generation, ρ represents an luciferin decay constant, ρ∈(0, 1), γ represents an luciferin enhancement constant, $F(x_i(t))$ represents an objective function value of the glowworm i at a current location $x_i(t)$, and the objective function is calculated according to the following equation:

$$F(x_i(t)) = \sum_{k=1}^{K} \frac{1}{d_{ik}(t)}$$

where $d_{ik}(t)$ represents a distance between the glowworm i at the current location $x_i(t)$ and the coordinates $E_k$ of the enterprise k, and can be expressed as $d_{ik}(t)=\|x_i(t)-E_k\|$.

S204: movement of the glowworm:

For each glowworm i, a moving probability $p_{ij}(t)$ to another glowworm j in its neighborhood $N_i(t)$ is calculated as:

$$p_{ij}(t) = \frac{L_j(t) - L_i(t)}{\sum_{k \in N_i(t)} L_k(t) - L_i(t)}$$

where a neighborhood set is $N_i(t)=\{j:d_{ij}(t)<r_d^i(t);L_i(t)<L_j(t)\}$, $d_{ij}(t)$ represents a distance between current locations of the t-th generation glowworms i and j, $r_d^i(t)$ represents a neighborhood radius of the glowworm i of the t-th generation, $0<r_d^i(t) \leq r_s$, $r_s$ represents a sensor radius of the glowworm, and $L_j(t)$ represents a luciferin of the glowworm i of the t-th generation.

The glowworm j, to which the glowworm i is to move for this time, is selected using the roulette rule, and marked with j', and then the location of the glowworm i is updated according to the following equation:

$$x_i(t+1) = x_i(t) + s\left(\frac{x_{j'}(t) - x_i(t)}{\|x_{j'}(t) - x_i(t)\|}\right) + \Delta_{attribute} + \Delta_{wind}$$

where $x_{j'}(t)$ represents a location of the glowworm j' of the t-th generation, represents a movement step size, and $\|\ \|$ represents solving an Euclidean norm.

$\Delta_{attribute}$ is a glowworm similarity correction factor introduced in the present invention considering the attribute of the glowworm, representing a displacement determined by a similar attribute of two glowworms, and calculated as follows: firstly in a neighborhood $N_i(t)$ of the glowworm i, a glowworm j* with a closest attribute value $A_j$ to the glowworm i is searched, that is, $j^* = \{j : \min|A_j - A_i|\}$; and then the glowworm similarity correction factor is calculated as:

$$\Delta_{attribute} = s_a \cdot \left(\frac{x_{j*}(t) - x_i(t)}{\|x_{j*}(t) - x_i(t)\|}\right)$$

where $s_a$ represents a predetermined step size, $x_{j*}(t)$ is a location of the glowworm j* of the t-th generation.

$\Delta_{wind}$ is a wind speed and direction correction factor introduced in the present invention by considering the influence of the wind power, representing a moving distance determined by the wind, and its calculation is as follows:

$$\Delta_{wind} = s_w \cdot \overrightarrow{speed}_{wind}$$

where $s_w$ is a scaling factor, i.e. a ratio between a wind speed unit and a resolution of a gridded remote sensing image. For example, when the resolution of the gridded remote sensing image is 5 km, that is, the length of a side of each grid is 5 km, and a wind speed unit is m/s, then the scaling factor is $s_w = 0.0002$.

S205: determining whether the iteration number t=T, T representing the maximum predetermined iteration number, if yes, proceed to step S206, otherwise, proceed to step S207.

S206: obtaining a source location of the glowworm:

A current location of each glowworm is taken as its source position $x_i^0$, and the iteration is terminated.

S207: updating the neighborhood radius.

In GSO, the neighborhood radius of each glowworm is not a constant, instead, it will be updated after each iteration. It is updated as follows:

$$r_d^j(t+1) = \min\{r_s, \max\{0, r_d^j(t) + \beta(n_t - |N_i(t)|)\}\}$$

where $\beta$ is a constant parameter for controlling a speed of updating the neighborhood, $n_t$ represents a neighborhood number control parameter, $|N_i(t)|$ represents the number of glowworms in the neighborhood set.

S208: letting t=t+1, and returning to the step S203.

It can be seen from the method for tracing pollution sources based on the GSO that the similarity of the AOD values and the effect of the wind power are considered in the present invention. By means of the GSO algorithm, the glowworms representing the pollutants are made to gradually move towards their sources, so as to realize the pollution source tracing. After identifying the pollution source, the following steps are performed.

S106: calculating a pollution coverage area of the enterprise:

Based on the coordinates $E_k$ of the image block corresponding to the enterprise, a radius $R_k$ of the pollution coverage area of the enterprise is obtained. A calculation method used in the present example is as follows: for the enterprise k, firstly an enterprise k' closest thereto is searched, and a distance $D_{kk'}$ between the two enterprises is calculated, $R_k = 0.5 D_{kk'}$.

S107: determining an enterprise producing the pollutants:

According to the radius $R_k$ of the pollution coverage area and the source location $x_i^0$ of each glowworm, the enterprise k is taken as the enterprise producing the pollutants corresponding to the glowworms in its pollution coverage area, and an AOD value corresponding to the glowworms in their pollution coverage area is calculated, as a pollution index of the enterprise k. According to the pollution index, the pollution situation of this enterprise can be evaluated. There are three types of pollution indices used in the present example: a total pollution gross a pollution intensity and an area normalization pollution.

The total pollution gross represents a summation of the AOD values of pollution sites around the pollution source enterprise. The total pollution gross $PG_k$ corresponding to the enterprise k is calculated as follows:

$$PG_k = \sum_{w=1}^{W_k} X_w^0$$

where $W_k$ is the number of glowworms in the pollution coverage area of the enterprise k, $x_w^0$ is an AOD value of a glowworm w in the pollution coverage area of the enterprise k.

The pollution intensity represents an average value of the AOD values of the pollution sites around the pollution source enterprise. The pollution intensity $PI_k$ corresponding to the enterprise k is calculated as follows:

$$PI_k = \frac{1}{W_k} \sum_{w=1}^{W_k} X_w^0 = \frac{1}{W_k} PG_k$$

Considering that enterprises are not evenly distributed, some enterprises are more isolated, and some are more aggregated, and sometimes isolated enterprises might attract pollution sites. In order to avoid such influence, an area normalization pollution index is proposed. A calculation formula of the area normalization pollution $ANP_k$ corresponding to the enterprise k is as follows:

$$ANP_i = \frac{\sum_k^n a_k}{\ln(area_i)} = \frac{PG_i}{\ln(area_i)}$$

where $area_k$ is the pollution coverage area of the enterprise k, the area was divided using Thiessen Polygons algorithm.

Figure 3:
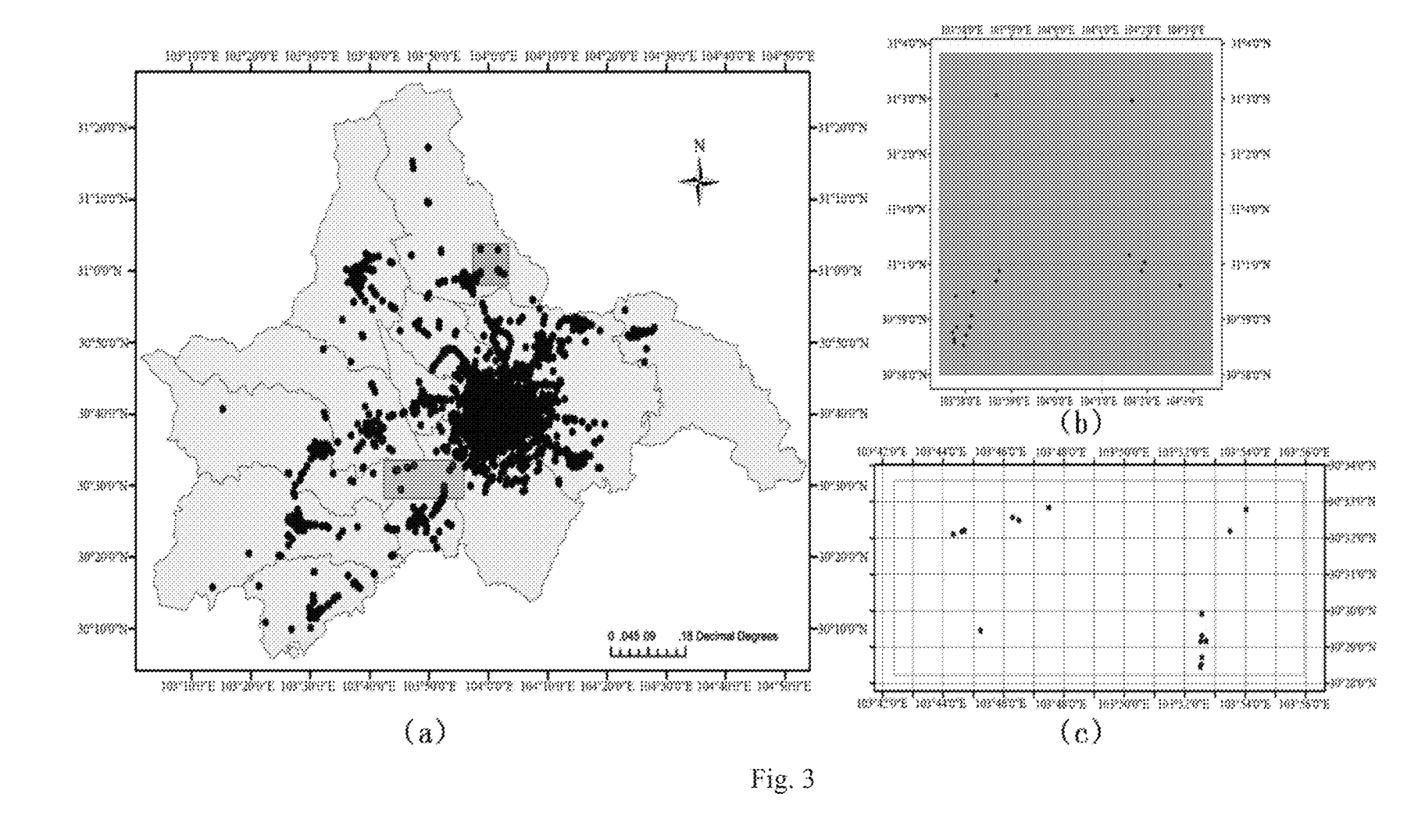
FIG. 3 is a regional map of Chengdu city.

In order to illustrate technical effects of the present invention, experiments are performed on the city of Chengdu as a verification of the effect of the present invention. Chengdu's prominent climate features include being cloudy, smoggy, having short sunshine duration, and high air humidity, and has an enclosed geographic environment as it is located in the middle of Sichuan Basin. As a result, air pollutants cannot be quickly scattered; instead, they can easily aggregate in the city and its outskirts. FIG. 3(a) is a map of Chengdu city. As shown in FIG. 3(a), in the present experimental verification, two districts of Dujiangyan (FIG. 3(b)) and Xinjin (FIG. 3(c)) of Chengdu are chosen as experimental areas. According to the updating date of GIS data, remote sensing data of h04/V30 based on MODIS L1B product (mod 021 km) on Mar. 17, 2009 is acquired as experimental data. GIS information for the enterprises in the studied area is up to 2009.

Figure 4:
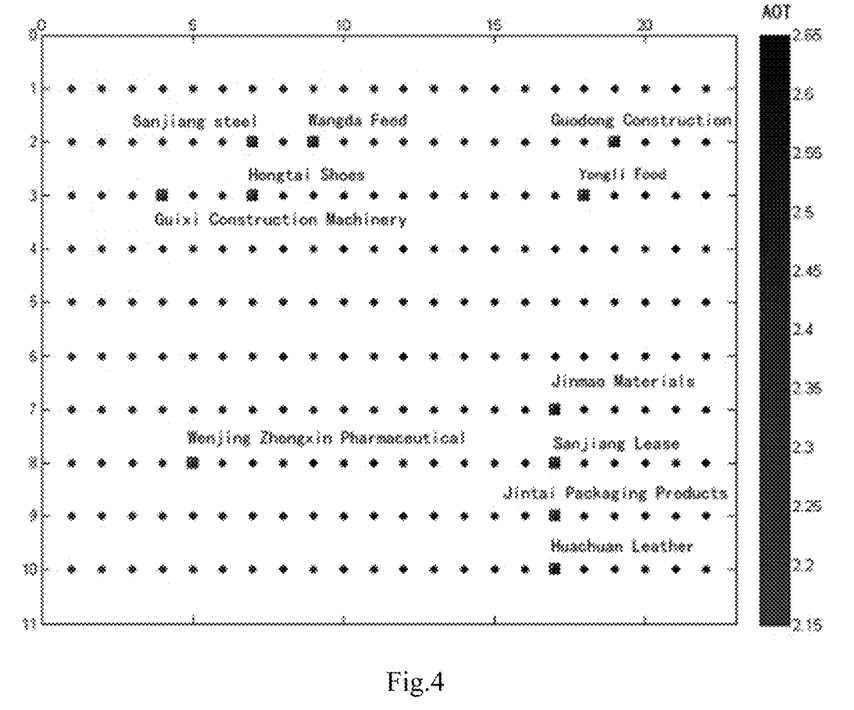
FIG. 4 is a gridded image of AOD values of Dujiangyan area.
Figure 5:
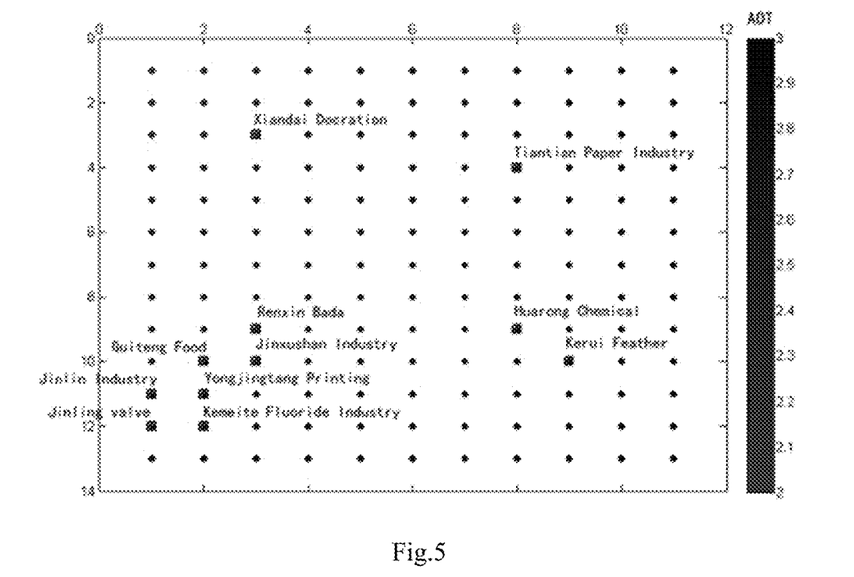
FIG. 5 is a gridded image of AOD values of Xinjin area.

Firstly the AOD values are retrieved using the conventional aerosol retrieval algorithm DDV, the resolution for retrieving the aerosol is 1 km; then gridding is performed. The location of the enterprise can be obtained by converting a GIS vector point into grid points of a TIF format. FIG. 4 is a gridded diagram of AOD values of Dujiangyan area. FIG. 5 is a gridded diagram of AOD values of Xinjin area. As shown in FIGS. 4 and 5, each dot represents one AOD value, and each small square represents one enterprise.

Then the pollution sources are traced using the GSO algorithm. Parameters of the GSO algorithm are set as follows: each glowworm has an initial luciferin value $L_i(0)=2$, a sensor range $r_s=2$, a self-adaptive decision domain initial value $r_d^i(0)=2$, a neighborhood threshold value $n_t=2$, a parameter $\beta=0.08$, a moving step size $s=s_a=0.03$, a luciferin decay constant $\rho=0.2$, a luciferin enhancement constant $\gamma=0.6$, and a maximum iteration number $T=200$.

Next, the pollution coverage areas of respective enterprises are calculated, and then the pollutants corresponding to the glowworms in their pollution coverage areas are obtained, as their sources.

Figure 6:
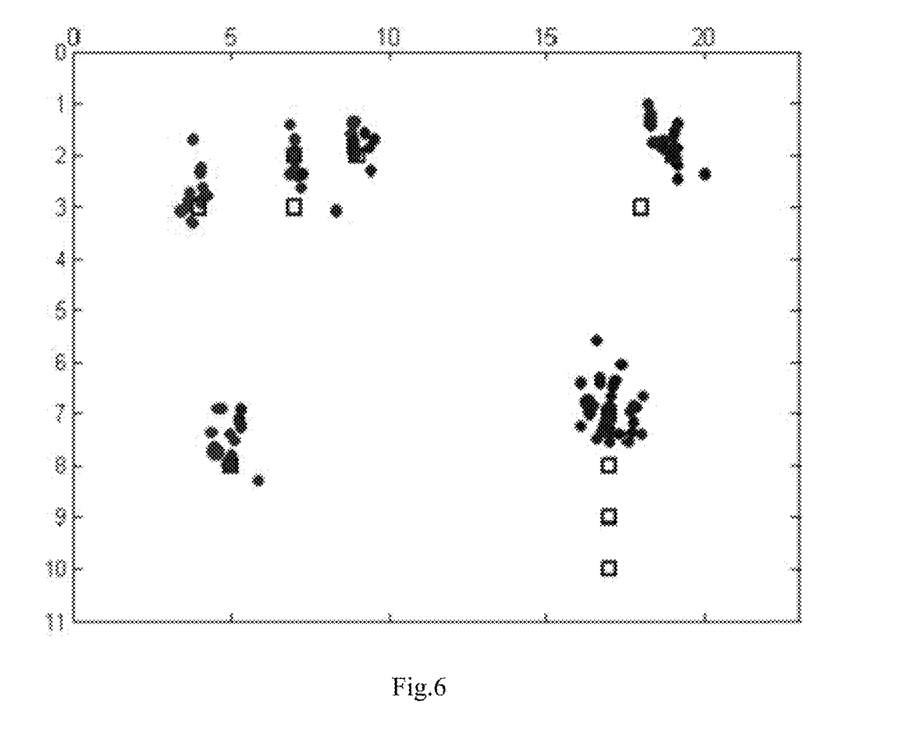
FIG. 6 is a diagram of tracing pollution sources in Dujiangyan area.
Figure 7:
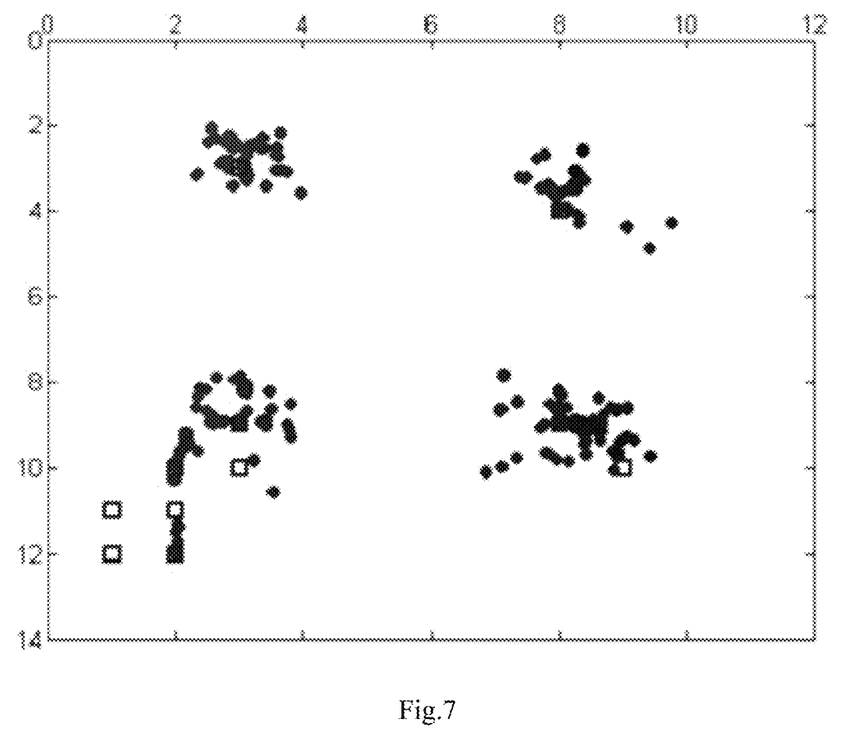
FIG. 7 is a diagram of tracing pollution sources in Xinjin area.

FIG. 6 is a diagram of traced pollution sources in Dujiangyan area. FIG. 7 is a diagram of traced pollution sources in Xinjin area. As shown in FIGS. 6 and 7, by tracing the pollution sources based on the GSO, the pollutants are concentrated to respective enterprises, so that the sources of the pollutants can be very easily determined.

Then the AOD value corresponding to the glowworms in its pollution coverage area, and the pollution indices of respective enterprises are calculated. Table 1 is pollution indices of 11 enterprises in Dujiangyan area.

TABLE 1

| Enterprises | Total pollution | Pollution | Area normalization |
|---|---|---|---|
| A1 | 36.31 | 2.24 | 1.28 |
| A2 | 38.83 | 2.30 | 0.49 |
| A3 | 42.12 | 2.32 | 13.41 |
| A4 | 9.39 | 2.34 | 2.99 |
| A5 | 42.71 | 2.39 | 3.40 |
| A6 | 62.74 | 2.50 | 19.97 |
| A7 | 9.48 | 2.23 | 3.02 |
| A8 | 0 | 0 | 0 |
| A9 | 0 | 0 | 0 |
| A10 | 0 | 0 | 0 |
| A11 | 65.78 | 2.51 | 20.94 |

Table 2 are indices of 11 enterprises in Xinjin area.

TABLE 2

| Enterprises | Total pollution gross | Pollution intensity | Area normalization pollution |
|---|---|---|---|
| B1 | 0 | 0 | 0 |
| B2 | 0 | 0 | 0 |
| B3 | 10.63 | 0.72 | 3.38 |
| B4 | 6.27 | 1.01 | 2.00 |
| B5 | 13.63 | 2.02 | 4.34 |
| B6 | 40.80 | 2.24 | 0.52 |
| B7 | 41.40 | 2.41 | 13.18 |
| B8 | 4.07 | 2.04 | 1.30 |
| B9 | 40.86 | 2.52 | 0.52 |
| B10 | 57.21 | 2.66 | 18.21 |
| B11 | 9.17 | 2.51 | 2.92 |

It can be seen from Table 1 and Table 2 that the pollution level of the enterprise A11 in Dujiangyan area is the highest, and all of its total pollution gross, pollution intensity and area normalization pollution are the highest, while the pollution level of the enterprise B10 in Xinjin area is the highest. It can be seen that by setting the threshold values of the three pollution indices, according to the pollution indices corresponding to respective enterprises calculated and obtained in the present invention, the pollution levels of respective enterprises can be easily determined, and severe pollution enterprises are identified.

The above is only the preferred embodiments of the invention and is not intended to limit the invention. For a person skilled in the art, the invention may have a variety of changes and modifications. Any change, equivalent replacement, improvement made within the spirit and principle of the present invention should be included in the protection scope of the invention

The invention claimed is:
1. A method for identifying air pollution sources based on aerosol retrieval and a glowworm swarm algorithm, comprising steps of:
    S1: acquiring a satellite remote sensing image and a digital map of a corresponding region;
    S2: acquiring a wind direction and a wind speed of the corresponding region of the satellite remote sensing image, to obtain a wind speed vector $\overrightarrow{speed}_{wind}$;
    S3: retrieving (Aerosol Optical Depth) AOD values from the satellite remote sensing image, to obtain an AOD result image;
    S4: gridding the AOD result image into M×N image blocks, calculating an average AOD value of pixels included in each image block; gridding the digital map of the corresponding region into M×N image blocks, obtaining coordinates $E_k$ of an image block corresponding to an enterprise k based on enterprise coordinates, where k=1, 2, . . . , K, and K represents the number of enterprises;
    S5: tracing pollutant sources using a method based on (Glowworm Swarm Optimization) GSO, which comprises steps of:
    S5(1): setting an initial luciferin level $L_i(0)$ of each glowworm to be the same, taking coordinates of each pixel block as an initial location $x_i(0)$ of the glowworm, taking an average AOD value corresponding to the pixel blocks as an attribute value $A_i$ of the glowworm, and setting an initial value $r_d^i(0)$ of a neighborhood of each glowworm, i=1, 2, . . . , Q, Q=M×N;
    S5(2): setting an iteration number t=1;
    S5(3): calculating a luciferin level of a glowworm of a t-th generation according to the following equation:

$$L_i(t)=(1-\rho)L_i(t-1)+\gamma F(x_i(t))$$

where t is the iteration number, i is an index of the glowworm, $L_i(t)$ is a luciferin level of a glowworm i of the t-th generation, $L_i(t-1)$ is a luciferin level of the glowworm i of a (t−1)-th generation, ρ is a luciferin decay constant, ρ∈(0,1), γ is a luciferin enhancement constant, $F(x_i(t))$ is an objective function value of the glowworm i at a current location $x_i(t)$, and the objective function is calculated according to the following equation:

$$F(x_i(t)) = \sum_{k=1}^{k} \frac{1}{d_{ik}^2(t)}$$

where $d_{ik}(t)$ is a distance between the glowworm i at the current location $x_i(t)$ and the coordinates $E_k$ of the enterprise k;

S5(4): for each glowworm i, respectively calculating a moving probability $p_{ij}(t)$ to another glowworm j in a neighborhood $N_i(t)$ thereof; selecting the glowworm j, to which the glowworm i is to move for this time, using a roulette rule, and marking with an index j', and then updating the location of the glowworm i according to the following equation:

$$x_i(t+1) = x_i(t) + s\left(\frac{x_{j'}(t) - x_i(t)}{\|x_{j'}(t) - x_i(t)\|}\right) + \Delta_{attribute} + \Delta_{wind}$$

where $x_{j'}(t)$ is a location of the glowworm j' of the t-th generation, S is a moving step size, and ∥ ∥ represents solving an Euclidean norm;

$\Delta_{attribute}$ is a glowworm similarity correction factor calculated as follows: firstly in a neighborhood $N_i(t)$ of the glowworm i, a glowworm j* with a closest attribute value $A_i$ to the glowworm i is searched and then $\Delta_{attribute}$ is calculated:

$$\Delta_{attribute} = s_a \cdot \left(\frac{x_{j*}(t) - x_i(t)}{\|x_{j*}(t) - x_i(t)\|}\right)$$

where $s_a$ is a predetermined step size, $x_{j*}(t)$ is a location of the glowworm j* of the t-th generation;

$\Delta_{wind}$ is a wind speed and wind direction correction factor, and calculated as: $\Delta_{wind} = s_w \cdot \overrightarrow{speed}_{wind}$, where $s_w$ is a scaling factor;

S5(5): in condition that the iteration number t=T, T being a maximum predetermined iteration number of times, taking a current location of each glowworm as a source location $X_i^0$ thereof, and terminating the iteration; otherwise proceeding to step S5(6);

S5(6): updating a neighborhood radius $r_d^i(t+1)$ of each glowworm, then letting t=t+1, and returning to step S5(3);

S6: obtaining a radius $R_k$ of a pollution coverage area of the enterprise according to the coordinates $E_k$ of the image block corresponding to the enterprise;

S7: according to the radius $R_k$ of the pollution coverage area and the source location $x_i^0$ of each glowworm, taking the enterprise k as an enterprise producing pollutants corresponding to the glowworms in the pollution coverage area thereof, calculating an AOD corresponding to the glowworms in the pollution coverage area thereof;

identifying the enterprise k as a pollution source;

determining a pollution index of the enterprise k, wherein the pollution index represents a pollution level of the enterprise k; and using the determined pollution index to evaluate a pollution situation of the enterprise k.

2. The method for identifying air pollution sources according to claim 1, wherein the moving probability $p_{ij}(t)$ in the step S5(4) is calculated as follows:

$$p_{ij}(t) = \frac{L_j(t) - L_i(t)}{\sum_{k \in N_i(t)} [L_k(t) - L_i(t)]}$$

where a neighborhood set is $N_i(t) = \{j : d_{ij}(t) < r_d^i(t); L_i(t) < L_j(t)\}$, $d_{ij}(t)$ is a distance between current locations of the glowworms i and j, $r_d^i(t)$ is a neighborhood radius of the glowworm i of the t-th generation, $0 < r_d^i(t) \le r_s$, $r_s$ is a sensor radius of the glowworm, and $L_j(t)$ is a luciferin level of the glowworm j of the t-th generation.

3. The method for identifying air pollution sources according to claim 1, wherein the neighborhood radius $r_d^i(t+1)$ in the step S5(6) is calculated as follows:

$r_d^i(t+1) = \min\{r_s, \max\{0, r_d^i(t) + \beta(n_t - |N_i(t)|)\}\}$ where β is a constant parameter, $n_t$ represents an area number control parameter.

4. The method for identifying air pollution sources according to claim 1, wherein in the step S6 the radius $R_k$ is calculated as follows: as to the enterprise k, firstly searching for an enterprise k' closest thereto, and calculating a distance $D_{kk'}$ between the two enterprises, $R_k = 0.5 D_{kk'}$.

5. The method for identifying air pollution sources according to claim 1, wherein the pollution index is a total pollution gross $PG_k$, and calculated as:

$$PG_k = \sum_{w=1}^{W_k} X_w^0$$

where $W_k$ represents the number of glowworms in the pollution coverage area of the enterprise k, $X_w^0$ represents an AOD value of a glowworm w in the pollution coverage area of the enterprise k.

6. The method for identifying air pollution sources according to claim 1, wherein the pollution index is a pollution intensity $PI_k$, and calculated as:

$$PI_k = \frac{1}{W_k} \sum_{w=1}^{W_k} X_w^0.$$

7. The method for identifying air pollution sources according to claim 1, wherein the pollution index is area normalization pollution $ANP_k$, and calculated as:

$$ANP_i = \frac{\sum_k^n a_k}{\ln(area_i)} = \frac{PG_i}{\ln(area_i)}$$

where $area_k$ is the pollution coverage area of the enterprise k.

* * * * *